US007996060B2

(12) United States Patent
Trofimov et al.

(10) Patent No.: US 7,996,060 B2
(45) Date of Patent: *Aug. 9, 2011

(54) APPARATUS, METHOD, AND COMPUTER SOFTWARE PRODUCT FOR REGISTRATION OF IMAGES OF AN ORGAN USING ANATOMICAL FEATURES OUTSIDE THE ORGAN (75) Inventors: Valery Trofimov, Haifa (IL); Assaf Preiss, Shimshit (IL); Gal Hayam, Tivon (IL)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/865,951

(22) Filed: Oct. 2, 2007

(65) Prior Publication Data
US 2008/0085042 A1    Apr. 10, 2008

Related U.S. Application Data (60) Provisional application No. 60/828,703, filed on Oct. 9, 2006.

(51) Int. Cl.
*A61B 5/05* (2006.01)
(52) U.S. Cl. .................. 600/424; 382/128; 345/630
(58) Field of Classification Search .................. 382/128, 382/173; 600/374, 381, 424, 427, 438, 467, 600/505, 509, 521; 345/420, 606, 621, 265, 345/630
See application file for complete search history.

(56) References Cited

U.S. PATENT DOCUMENTS

| 5,568,384 | A  |    | 10/1996 | Robb et al. |
| 6,332,089 | B1 |    | 12/2001 | Acker et al. |
| 6,563,941 | B1 | *  | 5/2003  | O'Donnell et al. ........... 382/131 |
| 6,618,612 | B1 |    | 9/2003  | Acker et al. |
| 6,650,927 | B1 | *  | 11/2003 | Keidar .......................... 600/424 |
| 6,690,816 | B2 |    | 2/2004  | Aylward et al. |
| 6,690,963 | B2 |    | 2/2004  | Ben-Haim et al. |
| 2002/0065455 | A1 |  | 5/2002  | Ben-Haim et al. |
| 2004/0068178 | A1 |  | 4/2004  | Govari |
| 2004/0147920 | A1 |  | 7/2004  | Keidar |
| 2006/0241445 | A1 |  | 10/2006 | Altmann et al. |

OTHER PUBLICATIONS

Parker et al. Image Based 3D Solid Model Construction of Human Arteries for Blood Flow Simulations. Proceedings of the 20th Annual International Conference of the IEEE Engineering in Medicine and Biology Society. 20(2) : p. 998-1001. 1998.*
Campagna et al. Enhancing digital documents by including 3-D models. Computers & Graphics. 22(6):655-666. Dec. 1998.*
Aylward et al. Registration and Analysis of Vascular Images, International Journal of Computer Vision 55:2-3, Nov.-Dec. 2003, pp. 123-138. (Abstract).

(Continued)

*Primary Examiner* — Parikha S Mehta
(74) *Attorney, Agent, or Firm* — Louis J. Capezzuto (57) ABSTRACT A method for imaging includes receiving a first three-dimensional (3D) image of a vicinity of an organ within a body of a subject and creating a geometrical model of a tubular structure in the first 3D image in the vicinity of the organ. An invasive probe is inserted into the organ, and a second 3D image containing the organ is captured using the invasive probe. One or more points are located on a surface of the tubular structure using the invasive probe, and the second 3D image is registered with the first 3D image by matching the one or more points to the geometrical model.

29 Claims, 7 Drawing Sheets

OTHER PUBLICATIONS

Gepstein, L. et al. A Novel Method for Nonfluoroscopic Catheter-Based Electroanatomical Mapping of the Heart in Vitro and in Vivo Accuracy Results, Circulation, vol. 95, No. 6, pp. 1611-1622, Mar. 1997.

Makela, T. et al. A Review of Cardiac Image Registration Methods, IEEE Transactions on Medical Imaging, vol. 21, No. 9, pp. 1011-1021, Sep. 2002.

Nollo, G. et al. Registration and Fusion of Segmented Left Atrium CT Images and Carto Electrical Maps for the Ablative Treatment of Atrial Fibrillation, Computers in Cardiology, IEEE, pp. 345-348, 2004.

Solomon, S.B. et al. Real-Time Cardiac Catheter Navigation on Three-Dimensional CT Images, Journal of Interventional Cardiac Electrophysiology, Journal of Interventional Cardiac Electrophysiology: An International Journal of Arrhythmias and Pacing, vol. 8, No. 1, pp. 27-36, Feb. 2003.

Su, Y. et al. A Piecewise Function-To-Structure Registration Algorithm for Image Guided Cardiac Catheter Ablation, Proceedings of the SPIE—The Optical Engineering SPIE—The International Society for Optical Engineering USA, vol. 6141, Feb. 2006.

Sun, Y. et al. Registration of High-Resolution 3D Atrial Images with Electroanatomical Cardiac Maping: Evaluation of Registration Methodology, Progress in Biomedical Optics and Imaging 2005—Visualization, Image-Guided Procedures, and Display 2005 SPIE US, vol. 5744, No. 1, pp. 299-307, 2005.

EP Search Report No: EP 07 25 3991 Dated Jun. 30, 2010.

* cited by examiner

APPARATUS, METHOD, AND COMPUTER SOFTWARE PRODUCT FOR REGISTRATION OF IMAGES OF AN ORGAN USING ANATOMICAL FEATURES OUTSIDE THE ORGAN

CROSS-REFERENCE TO RELATED APPLICATION

This application claims the benefit of U.S. Provisional Patent Application 60/828,703, filed Oct. 9, 2006, which is incorporated herein by reference.

FIELD OF THE INVENTION

The present invention relates generally to image processing, and specifically to methods and systems for analysis and display of medical images.

BACKGROUND OF THE INVENTION

In some medical imaging applications, images from different sources, which are generated using multiple modalities, are registered with one another and displayed. For example, U.S. Pat. No. 5,568,384, whose disclosure is incorporated herein by reference, describes a method for synthesizing 3-D multimodality image sets into a single composite image. Surfaces are initially extracted from two or more different images to be matched using semi-automatic segmentation techniques. The surfaces are represented as contours with common features to be matched. A matching process involves searching the multi-parameter space and adjusting a surface or surfaces to find the best fit among them. Makela, et al., survey methods of image registration in "A Review of Cardiac Image Registration Methods," *IEEE Transactions on Medical Imaging* 21:9 (September 2002), pages 1011-1021, which is incorporated herein be reference.

Aylward, et al., describe methods for processing of tubular objects in medical images in U.S. Pat. No. 6,690,816 and in "Registration and Analysis of Vascular Images," *International Journal of Computer Vision* 55:2-3 (November-December 2003), pages 123-138, both of which are incorporated herein by reference. They point out that registration of tubular objects in multi-dimensional images may be helpful in medical imaging applications. This sort of tubular object registration aligns the image elements of tubular objects between a source image and a destination image, which may be produced using different image modalities. The patent gives an example of the registration of pre-operative CT or MR data with intra-operative ultrasound data for radio-frequency ablation treatment of liver lesions.

SUMMARY OF THE INVENTION

Embodiments of the present invention that are described hereinbelow provide methods and systems for registering different medical images of an organ using anatomical features outside the organ. The term "image" is used broadly in the context of the present patent application and in the claims to mean any three-dimensional (3D) representation of the shape or contours of the organ. The methods that are described hereinbelow may be used to register images that are captured using different modalities, such as registering a pre-acquired 3D image of an organ with a 3D representation of the organ created in real time by an invasive probe within the organ.

In some embodiments, tubular structures outside the organ, such as blood vessels, are used in registering the images. Tubular structures may be identified in 3D images using a fast, accurate method that is described hereinbelow, based on the segmented surface of the tubular structure. Since invasive probes for treating organs, such as cardiac catheters, are often inserted into the target organ through a blood vessel, a real-time image of the blood vessel may be created, using the probe, during passage of the probe through the vessel. This image may be registered with the corresponding blood vessel in the pre-acquired image, so that the frame of reference of the probe is registered with the pre-acquired image before the probe even enters the target organ.

Alternatively or additionally, a human operator may interactively indicate landmarks outside the target organ in the pre-acquired image, using a pointing device to mark the relevant points on a display, for example. The operator may then indicate the corresponding points in the real-time image, possibly by bringing the probe into physical contact with the landmark locations. Referring again to the example of blood vessels mentioned above, the landmarks may be locations in the aorta or vena cava, and the operator may bring the probe into contact with these locations as the probe passes through the vessel in question on the way into the heart.

There is therefore provided, in accordance with an embodiment of the present invention, a method for imaging, including:

receiving a first three-dimensional (3D) image of a vicinity of an organ within a body of a subject;

creating a geometrical model of a tubular structure in the first 3D image in the vicinity of the organ;

inserting an invasive probe into the organ;

capturing a second 3D image containing the organ using the invasive probe;

locating one or more points on a surface of the tubular structure using the invasive probe; and registering the second 3D image with the first 3D image by matching the one or more points to the geometrical model.

In some embodiments, locating the one or more points includes inserting the invasive probe into the tubular structure, and identifying the surface of the tubular structure while the invasive probe is inside the tubular structure. In one embodiment, identifying the surface includes bringing the probe into contact with the one or more points, and determining coordinates of the probe. Locating the one or more points may include receiving an input from a user marking the one or more points on the first 3D image. Alternatively or additionally, inserting the invasive probe into the tubular structure includes passing the invasive probe into the organ via the tubular structure. In a disclosed embodiment, the organ includes a heart of the subject, and the tubular structure through which the invasive probe is passed includes a blood vessel that communicates with a chamber of the heart.

In some embodiments, the geometrical model created of the tubular structure in the first 3D image is a first geometrical model, and locating the one or more points includes processing the second 3D image to create a second geometrical model of the tubular structure, and matching the one or more points includes fitting the second geometrical model to the first geometrical model. In a disclosed embodiment, capturing the second 3D image includes generating an anatomical map of an inner surface of the organ by bringing the probe into contact with an inner surface of the organ at multiple locations on the inner surface, and recording position coordinates of the probe at each of the locations. Generating the anatomical map may include producing an electro-anatomical map by measuring local electrical activity, using the probe, at the multiple locations, wherein registering the second 3D image with the first 3D image includes superimposing an indication of the local electrical activity on the first 3D image. Alternatively, capturing the second 3D image includes producing an ultrasound image of the organ using an ultrasound transducer in the probe, and locating the one or more points includes identifying the one or more points in the ultrasound image.

In a disclosed embodiment, locating the one or more points includes determining coordinates of the one or more points based on signals provided by a position sensor in the probe.

In one embodiment, the tubular structure is outside the organ, wherein the organ is a heart of the subject, and wherein the tubular structure includes a blood vessel in the vicinity of the heart.

There is also provided, in accordance with an embodiment of the present invention, a method for imaging, including:

receiving a three-dimensional (3D) image of a tubular structure within a body of a subject;

identifying a plurality of points appearing in the 3D image on a surface of the tubular structure;

defining rings, each ring passing through a respective subset of the points on the surface and encircling the tubular structure; and combining the rings to create a 3D geometrical model of the surface of the tubular structure.

Typically, defining the rings includes specifying a starting point, and incorporating in the respective subset for each ring a group of the points that are equidistant from the starting point.

There is additionally provided, in accordance with an embodiment of the present invention, apparatus for imaging, including:

an invasive probe, which is configured to be inserted into an organ within a body of a subject; and a processor, which is coupled to receive a first three-dimensional (3D) image of a vicinity of the organ and to create a geometrical model of a tubular structure in the first 3D image in the vicinity of the organ, and which is configured to capture a second 3D image containing the organ using the invasive probe, and to locate one or more points on a surface of the tubular structure using the invasive probe, and to register the second 3D image with the first 3D image by matching the one or more points to the geometrical model.

There is further provided, in accordance with an embodiment of the present invention, a computer software product, including a computer-readable medium in which program instructions are stored, which instructions, when read by a computer, cause the computer to receive a first three-dimensional (3D) image of a vicinity of an organ within a body of a subject, to create a geometrical model of a tubular structure in the first 3D image in the vicinity of the organ, to capture a second 3D image containing the organ using an invasive probe that is inserted into the organ, to locate one or more points on a surface of the tubular structure using the invasive probe, and to register the second 3D image with the first 3D image by matching the one or more points to the geometrical model.

There is moreover provided, in accordance with an embodiment of the present invention, a computer software product, including a computer-readable medium in which program instructions are stored, which instructions, when read by a computer, cause the computer to receive a three-dimensional (3D) image of a tubular structure within a body of a subject, to identify a plurality of points appearing in the 3D image on a surface of the tubular structure, to define rings, each ring passing through a respective subset of the points on the surface and encircling the tubular structure, and to combine the rings to create a 3D geometrical model of the surface of the tubular structure.

The present invention will be more fully understood from the following detailed description of the embodiments thereof, taken together with the drawings in which:

DETAILED DESCRIPTION OF EMBODIMENTS

System Description

Figure 1:
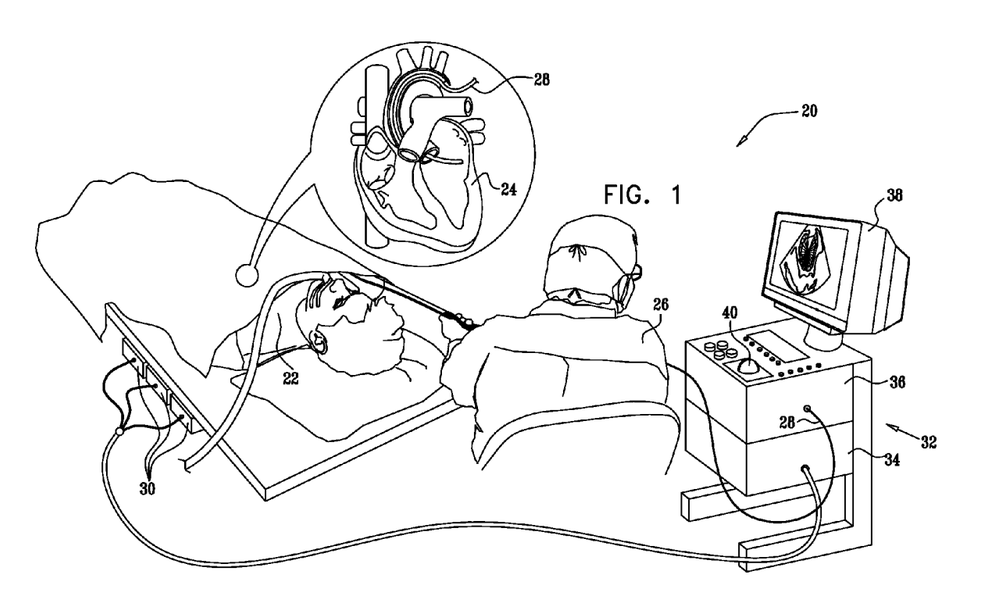
FIG. 1 is a schematic, pictorial illustration of a system for medical imaging, in accordance with an embodiment of the present invention.

FIG. 1 is a schematic, pictorial illustration of a system 20 for imaging a heart 24 of a patient 22, in accordance with an embodiment of the present invention. The system comprises a catheter 28, which is inserted by an operator 26, such as a physician, into a chamber of the heart through a vein or artery. System 20 comprises a positioning sub-system that measures position (location and orientation) coordinates of catheter 28.

In one embodiment, the positioning sub-system comprises a magnetic position tracking system, comprising a set of external radiators 30, which are located in fixed, known positions external to the patient. Coils 30 generate fields, typically electromagnetic fields, in the vicinity of heart 24. The generated fields are sensed by a position sensor 31 inside the distal end of catheter 28.

Some position tracking systems that may be used in this manner are described, for example, in U.S. Pat. Nos. 6,690,963, 6,618,612 and 6,332,089, and U.S. Patent Application Publications 2002/0065455 A1, 2004/0147920 A1 and 2004/0068178 A1, whose disclosures are all incorporated herein by reference. A tracking system of this sort is used in the CARTO™ system, which is produced by Biosense Webster Inc. (Diamond Bar, California). Alternatively, although the positioning sub-system shown in FIG. 1 uses magnetic fields, the methods described below may be implemented using any other suitable positioning sub-system, such as systems based on electromagnetic fields, electrical impedance measurements, or acoustic measurements.

Catheter 28 also comprises at least one transducer 33 at its distal end for use in creating images of heart 24. Transducer 33 may comprise, for example, an electrode, which measures electrical activity at points on the endocardium with which the tip of the catheter is brought into contact. Such an electrode, in combination with the position sensor, may be used in generating electro-anatomical maps of one or more chambers of the heart, as in the above-mentioned CARTO system, for example. Such maps are considered to be "images" in the context of the present patent application and in the claims, in accordance with the definition given above.

Additionally or alternatively, transducer 33 may comprise one or more ultrasound transducers, which are used in capturing intracardiac ultrasound images. The readings provided by position sensor 31 are used in registering the ultrasound images captured at different positions of the catheter (which may be two-dimensional or three-dimensional images) in order to reconstruct a full 3D image. This image may comprise one or more chambers of the heart, as well as nearby structures outside the heart, such as blood vessels. A catheter and system with such capabilities (and also including an electrode for electro-anatomical sensing) is described in U.S. Patent Application Publication 2006/0241445, whose disclosure is incorporated herein by reference.

Further additionally or alternatively, catheter 28 and system 20 may be adapted to create images of other types, such as maps showing mechanical activity or other types of physiological activity within the heart. Furthermore, although the embodiments described herein relate specifically to cardiac imaging, the principles of the present invention may similarly be applied to other organs of the body.

A console 32 drives and controls the elements of system 20. Console 32 comprises a radiator driver circuit 34, which generates signals to drive radiators 30. A signal processor 36 processes the signals that are output by catheter 28, including position signals output by sensor 31 and transducer signals output by transducer 33. The signal processor processes these signals in order to generate an image of heart 24, such as the 3D ultrasound image and/or the electro-anatomical map mentioned above. Typically this image is produced in real time, i.e., in the course of acquiring data using the catheter, while the operator maneuvers the catheter in the patient's body. (Alternatively, the methods described below may be applied after this image has been acquired.) The image is presented on an output device, such as a display 38. The operator may interact with the signal processor using a user input device, such as a trackball 40 or other pointing device.

In some embodiments, which are described in greater detail hereinbelow, signal processor 36 also receives a pre-acquired 3D image of heart 24. The image is "pre-acquired" in the sense that it was separately acquired using another imaging modality. Examples of such modalities include computed tomography (CT), magnetic resonance imaging (MRI), positron emission tomography (PET), and ultrasound imaging using an external probe. The signal processor processes both the pre-acquired image and the real-time image to register the real-time image with the pre-acquired image. Methods for performing this processing and registration are described in detail hereinbelow. The registered images may then be presented together on display 38. For example, anatomical and/or functional detail from the real-time image may be superimposed on the pre-acquired image.

Typically, signal processor 36 comprises a general-purpose computer, which has suitable input circuits for receiving the relevant image and position data, and which is programmed in software to carry out the functions that are described herein. This software may be downloaded to the computer in electronic form, over a network, for example. Alternatively or additionally, the software may be stored on tangible media, such as optical, magnetic or electronic memory media. Further additionally or alternatively, at least some of the functions of the signal processor may be carried out by dedicated or programmable signal processing circuitry.

Registration of Tubular Objects

Figure 2:
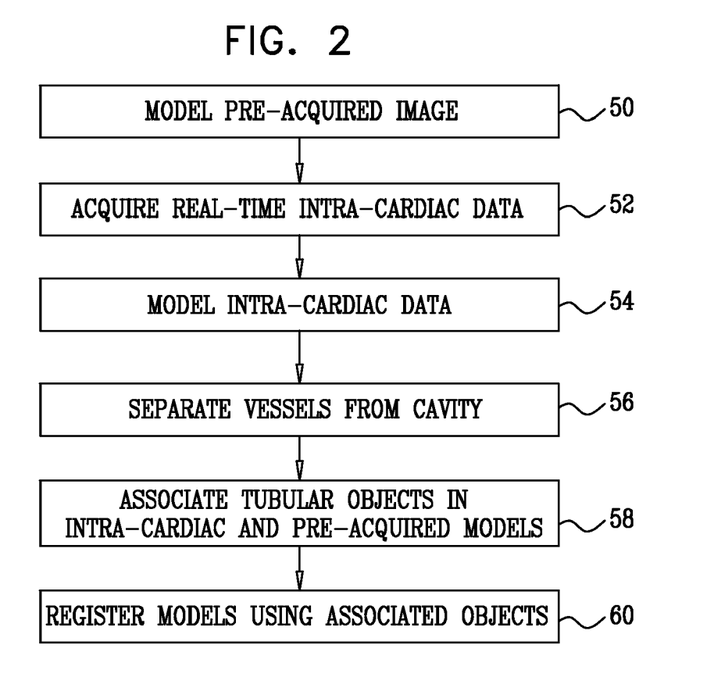
FIG. 2 is a flow chart that schematically illustrates a method for registering images of the heart, in accordance with an embodiment of the present invention.

FIG. 2 is a flow chart that schematically illustrates a method for registering a pre-acquired 3D image, such as a MRI, CT or PET image, acquired in an image coordinate system, with a real-time heart model created using a catheter with an electromagnetic position sensing system, such as catheter 28 in system 20. The real-time heart model is generated either by electro-anatomical contact mapping or intracardiac ultrasound imaging. Although the final result is a registered image of a heart chamber, the registration process is based on registering blood vessels of interest in the pre-acquired and real-time models. The blood vessels are not necessarily part of the heart itself.

Throughout the present patent application, the blood vessels used for registration are referred to as "tubular structures." Other tubular structures (not only blood vessels) may be used for registration in the same way. The following tubular structures, for example, can serve as objects for registration of images of the heart:

Inferior vena cava.
Superior vena cava.
Coronary sinus.
Coronary arteries.
Aorta.
Esophagus.
Pulmonary veins Registration of tubular structures is fast and accurate and enables the coordinates of an image of an organ of interest to be registered with the coordinate system of a catheter while the catheter is outside the organ. Thus, for example, in the method of FIG. 2, the heart chambers may be registered using vessels or other tubular structures that are outside the heart. The method does not rely on the volumetric data of the pre-acquired image, but rather uses the segmented surface of the tubular structure.

Since catheters are normally inserted into the heart through certain blood vessels, such as the vena cava or the aorta, the real-time image that is used in the method of FIG. 2 can be acquired during passage of the catheter through the vessel.

The pre-acquired image may then be pre-registered with the catheter frame of reference before the catheter even enters the heart. Real-time modeling of the blood vessel through which the catheter is passing provides the user with clear feedback regarding the shape of the vessel and the catheter location within it. This feature of the present embodiment enhances the safety and speed of the mapping procedure.

Moreover, as illustrated in the figures that follow, the method of FIG. 2 may be used to register several tubular structures simultaneously. The inventors have found that this simultaneous approach gives superior registration accuracy to use of only a single vessel or even sequential registration of several vessels. Simultaneous registration averages out possible errors that may be caused by deformation of the heart and surrounding tissue due to heart rhythm changes, as well as deformation of the soft tissue by the catheter during mapping.

The method of FIG. 2 can also provide automatic detection of the area of intersection of the tubular vessel model and the cavity of interest, such as the heart chamber with which the vessel communicates. This technique creates separate geometrical entities that may be used reliably for further diagnostic and/or therapeutic activity. For instance, detection of the intersection of the pulmonary veins with the left atrium, as illustrated in the figures that follow, allows the location of the ostium to be highlighted for use in planning a subsequent ablation procedure.

Turning now to the specifics of FIG. 2, the method begins with modeling of one or more tubular structures, such as blood vessels, in a pre-acquired image, at a first image modeling step 50. In some imaging modalities, such as CT, that may be used to provide the pre-acquired image, tubular structures, such as blood vessels, are often output as part of the segmentation of the main cavity with which they are associated. Furthermore, this segmentation may be provided as a mesh, rather than voxel data, and it may contain segmentation artifacts. Under these circumstances, modeling the tubular structures at step 50 is needed to enable the processor to properly identify and locate these structures. Details of this step are shown below in FIG. 3. The operator may designate the tubular structure in the pre-acquired image that is to be modeled, in order to reduce the likelihood of error due to incorrect segmentation, for example.

Catheter 28 is navigated through a region of interest within the body, and map points are acquired, inter alia, along the inner surface of a vessel that is to be modeled, at a real-time acquisition step 52. The map points may be created by bringing the tip of the catheter into contact with the inner surface of the vessel at locations of spatial and electrical stability. Alternatively or additionally, intra-cardiac contours of vessel(s) of interest may be acquired using an intra-cardiac ultrasound catheter equipped with a position sensor, as described above. In this mode of operation, each contour of the vessel that is acquired by the catheter is considered to comprise several map points.

Processor 36 constructs a vessel model in real-time from the cloud of map points, at a map modeling step 54. As noted earlier, in the context of the present patent application and the claims, this sort of map is considered to be an "image." Details of step 54 are shown below in FIG. 6.

The processor separates the vessel or vessels that is has modeled from the chamber of the heart that is of interest, at a vessel separation step 56. For this purpose, the processor identifies the ostium of the vessel, where the pulmonary veins enter the left atrium, for example, or where the aorta exits from the left ventricle. The purpose of this step is to resolve confusion that may arise in the mapping procedure when acquired map points that are part of the vessels are erroneously associated with the heart chamber and vice versa. For instance, pulmonary vein points may be erroneously identified as part of the left atrium, or aorta points may be identified as part of the left ventricle due to mistakes in the operator's workflow.

Step 56 is intended to correct such mistakes by automatically delineating the ostium. The ostium may be identified, for example, by detecting the intersection line of the meshes that correspond to the vessel (or vessels) and the chamber and identifying the part of the vessel mesh that is located inside the chamber. Triangles of the mesh that are crossed by the intersection line are divided, thus creating two separate meshes. The internal parts of each mesh are then removed. To make the meshes topologically consistent, holes are closed by triangulation.

Processor 36 associates each vessel modeled at steps 54 and 56 with the corresponding vessel in the model of the pre-acquired image from step 50, at an object association step 58. As noted earlier, several different vessels, such as the pulmonary veins, may be registered simultaneously at this step in order to provide more accurate results. The process of vessel identification and association is described further hereinbelow with reference to FIGS. 9 and 10. Although the process of vessel association is typically carried out automatically, the operator may optionally assist the automatic process, particularly when multiple vessels are involved, by pointing to pairs of vessels (in the pre-acquired image and in the map) that are to be associated with one another.

Based on the associated vessels, the processor registers the models created in steps 50 through 56, at a registration step 60. The models are registered initially by minimizing the distances between corresponding segments of the centerlines of the tubes that represent each pair of the vessels associated at step 58. Fine registration is then performed by rotating and translating the map to minimize the sum of squares of the signed distances of the mesh points generated at step 56 from the surface of the pre-acquired image model. The signed distance is negative for mesh points that are located inside the mesh of the model of the pre-acquired image. The distance for each of these inside points is set to zero in order to neutralize the possible influence of incomplete or one-sided mapping by the operator. Alternatively or additionally, the pre-acquired image model may be modified to fit the map model.

Figure 11:
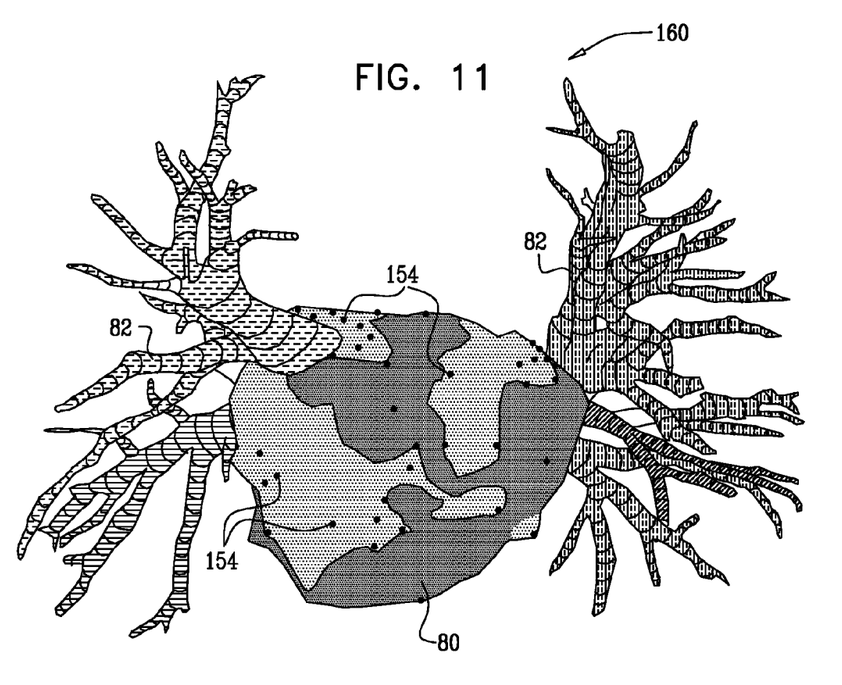
FIG. 11 is a schematic representation of a pre-acquired image of a left atrium, on which features of an electro-anatomical map of the left atrium have been superimposed following image registration in accordance with an embodiment of the present invention.

Following the registration procedure, the map data acquired at step 52 may be superimposed on the pre-acquired image. A superimposed image resulting from this sort of modeling and registration is shown in FIG. 11. A similar registration procedure can be repeated subsequently, if needed, at any time, based on new map points acquired by the operator. The registration accuracy can also be measured and displayed for the operator.

Figure 3:
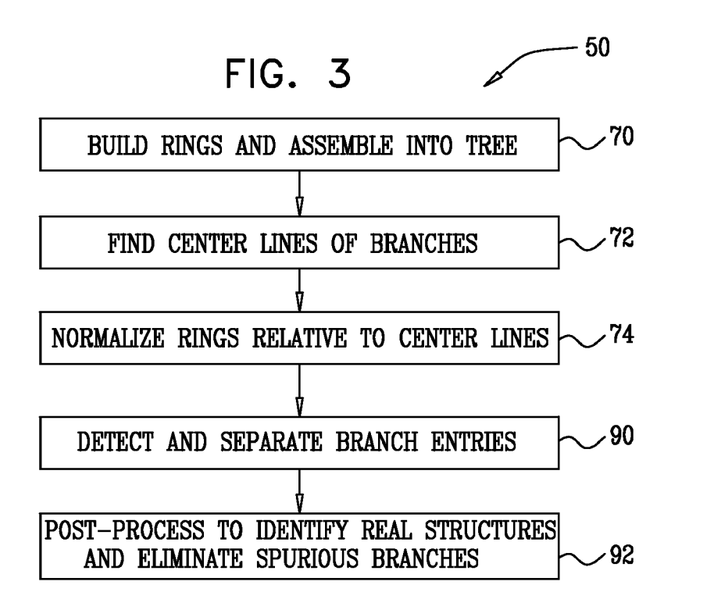
FIG. 3 is a flow chart that schematically illustrates a method for modeling tubular structures in a 3D image, in accordance with an embodiment of the present invention.

FIG. 3 is a flow chart that schematically shows details of a method that may be used at step 50 to model tubular structures in the pre-acquired image, in accordance with an embodiment of the present invention. This method models tubular structures based on the locations of points on the surface of the segmented object or contours in the pre-acquired image, and does not require voxel (location/intensity) data. Thus, the method is capable of receiving and operating on a segmented mesh input, as explained above, rather than the complete volume image as in some methods that are known in the art.

In preparation for the method of FIG. 3, processor 36 converts the pre-acquired image mesh to a half-edge data structure, which facilitates efficient 3D calculations. (Half-edge is an oriented edge that stores a pointer to its origin, a pointer to the facet to its left, a pointer to its target vertex, and a pointer to the opposite edge on the facet to its right.) To identify the main body of the model, the processor builds a set of rings encircling the outer surface of the volume in the image, at a ring building step 70. To build the rings, the processor starts from an arbitrary point within the volume that is to be modeled, and connects subsets of the points on the edges of the volume that are equidistant from the starting point. The starting point may be selected at random, automatically, without user intervention. The processor then makes topological connections between these edge points using relations between the half-edges and thus separates rings that belong to different vessel branches. Whenever several rings are defined at a given step from one initial ring, the processor creates two or more corresponding child nodes (branches). The processor arranges the branches in a tree structure.

To improve the modeling results, the processor now identifies the root of this tree, and builds a new set of rings using the root as the starting point (instead of the arbitrary point that was used in the first pass through the data). Based on these new rings, the processor rebuilds the tree and connects the centers of the rings to make a first approximation of the center lines of the branches, at a branch construction step 72. The processor then adjusts the rings so that they are orthogonal to these center lines, at a ring normalization step 74. Normalization and center line construction are repeated iteratively in order to produce a consistent model.

Figure 4:
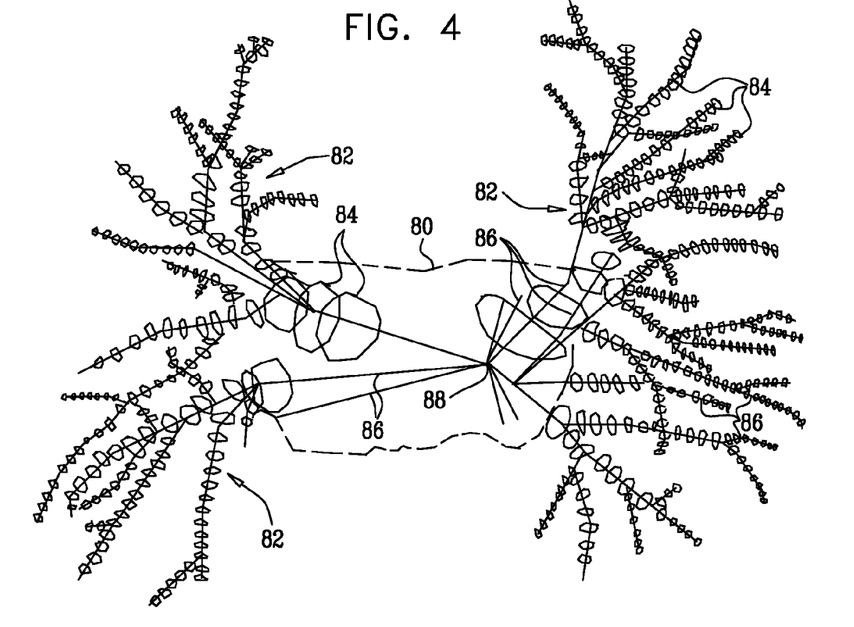
FIG. 4 is a schematic representation of rings and center lines representing blood vessels in a 3D model of a heart generated by the method of FIG. 3, in accordance with an embodiment of the present invention.

FIG. 4 is a schematic representation of a left atrium 80 following steps 72 and 74, in accordance with an embodiment of the present invention. The tree of pulmonary veins 82 is represented by rings 84 surrounding each of the veins and its subsidiary branches. Center lines 86 of the branches of the tree meet at a root 88.

Returning now to FIG. 3, processor 36 detects and separates the branch entry points, at a branch separation step 90. The "entry point" of a branch in this context refers to the base of the branch, including the entry points where the main branches separate from the main body. The entry points are first approximated based on the topology of the tree that was built at step 74. A surface analyzer algorithm is then used to identify the entry points precisely. This algorithm builds line strips on the surface of the volume along the intersection of the surface with planes rotated around the center line. Points with high angles of intersection are connected to produce the rings for branch entry. The processor separates the tubular structures (such as the pulmonary veins) from other parts of the volume using these rings.

In some cases, such as in modeling the left atrium and pulmonary veins, the processor performs an extra phase of post-processing to "clean up" the model, at a post-processing step 92. The processor identifies the pulmonary veins on the basis of known anatomy and the orientation of the pre-acquired 3D image. This step enables the processor to identify spurious branches, which may have been created as a result of inaccuracy in the segmentation process or anatomical features such as the left atrial appendage. The processor eliminates these branches from consideration as "tubular structures."

Figure 5:
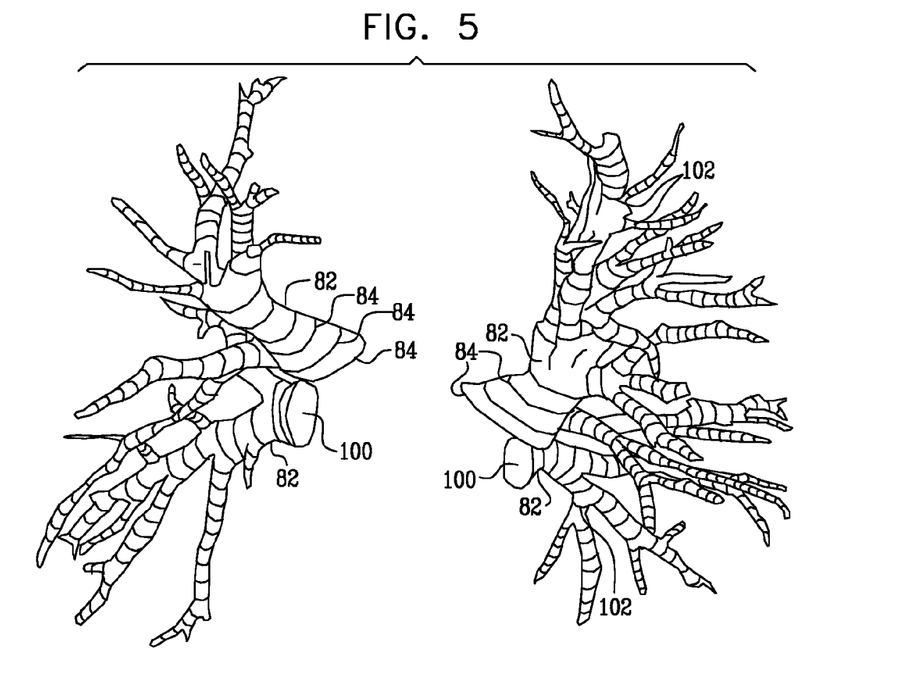
FIG. 5 is a schematic representation of a 3D model of the pulmonary veins of a heart generated by the method of FIG. 3, in accordance with an embodiment of the present invention.

FIG. 5 is a schematic representation of pulmonary veins 82 following completion of step 92, in accordance with an embodiment of the present invention. The representation is created by combining rings 84, which defined the vein topology. The left atrium itself has been removed from the model for clarity. The figure shows entry areas 100 where the main veins enter the left atrium, as well as entry points 102 where subsidiary veins branch from the main veins.

Figure 6:
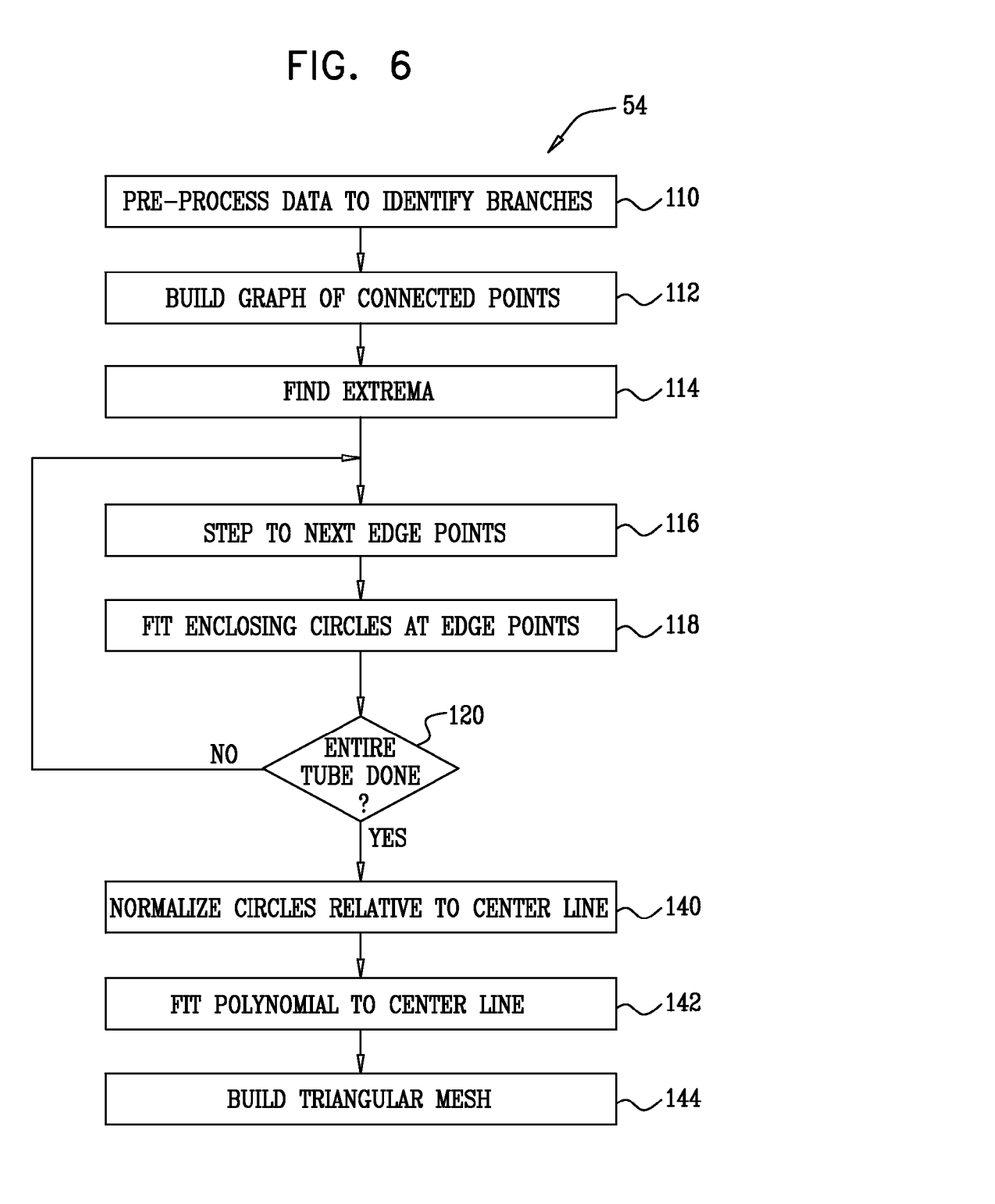
FIG. 6 is a flow chart that schematically illustrates a method for modeling tubular structures in an image created by an invasive probe, in accordance with an embodiment of the present invention.

FIG. 6 is a flow chart that schematically shows details of a method that may be used at step 54 to model the real-time intra-cardiac data acquired by catheter 28, in accordance with an embodiment of the present invention. This method operates on the set of map points on the surface of the tubular structure in question that are acquired using the catheter at step 52. If the tubular structure has branches, processor 36 identifies and separates them at a preprocessing step 110. For this purpose, the processor builds an oriented minimal-volume box containing the tubular structure. This box is divided into two minimal-volume oriented boxes if this split produces a significant reduction of volume, and the division of boxes into smaller boxes continues iteratively. Subsets of the map points are defined by projecting the collected points onto the closest planes that are orthogonal to a selected scan direction (which is typically parallel to the long axis of the box). Hierarchical clustering is used to identify clusters of points within each box that belong to different branches and to adjust branch limits accordingly. The subsequent steps in the method of FIG. 6 are then applied to model each branch separately, after which the branch models are merged into a model of the entire vessel tree.

For each branch, the processor builds a graph of connected points, at a graph construction step 112. Points are defined as connected if the distance between them is within a predetermined threshold. The processor automatically finds the extreme points of the graph, i.e., the points that are separated by the maximal distance, at an extrema definition step 114. Starting from one of these extreme points, the processor steps to the next edge points on the graph whose coordinates are within a predetermined step size of the extreme points, at an edge point selection step 116. The processor fits an enclosing circle (ring) around these edge points, at a circle fitting step 118. The processor then steps from these edge points to the next edge points (repeating the same step size) and fits another enclosing circle around them, continuing iteratively through steps 116 and 118 until it has reached the other extreme point, at a tube completion step 120. The processor defines a line connecting the centers of the circles created at step 118, and smoothes this line as a first approximation of the center line of the vessel.

Figure 7:
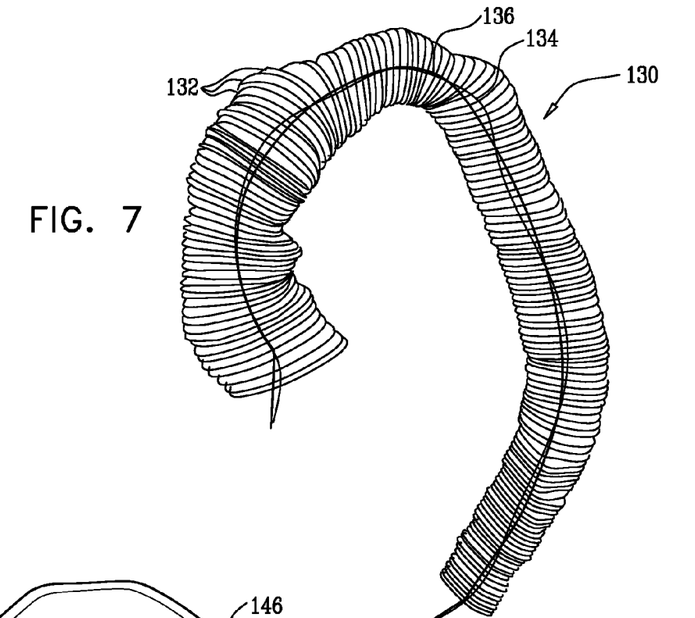
FIG. 7 is a schematic representation of rings and center lines representing a blood vessel in a 3D model of the vessel that was generated by the method of FIG. 6, in accordance with an embodiment of the present invention.

FIG. 7 is a schematic representation of circles 132 representing a blood vessel 130 in a 3D model of the vessel generated by the steps described above, in accordance with an embodiment of the present invention. In this example, the blood vessel is the aorta, showing the region of the aortic arch without branch vessels. An initial center line 134 connects the centers of the circles.

Returning to FIG. 6, processor 36 normalizes the circles, i.e., adjusts the circles so that they are orthogonal to the smoothed center line, at a normalization step 140. The processor then redefines the center line by fitting a polynomial curve to approximate the center line that was defined previously, at a fitting step 142. This curve provides an analytical representation of the center line, which may be used in refinement of the model. A polynomial center line 136 of this sort is shown in FIG. 7. Finally, the processor fits a triangular mesh over the circles to give the entire surface of the tubular structure, at a mesh building step 144.

Figure 8:
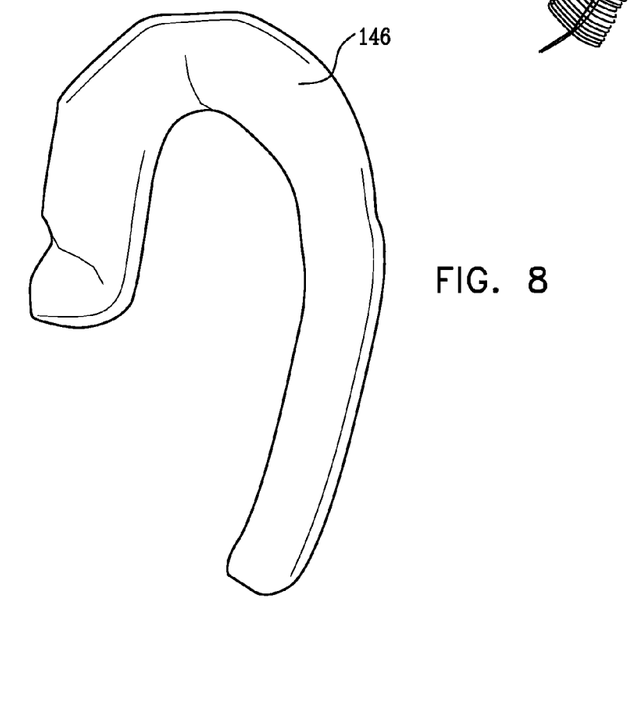
FIG. 8 is a schematic representation of a 3D model of a blood vessel generated by the method of FIG. 6, in accordance with an embodiment of the present invention.

FIG. 8 is a schematic representation of a triangular mesh surface 146 of the aorta that is created at step 144, in accordance with an embodiment of the present invention.

Figure 9:
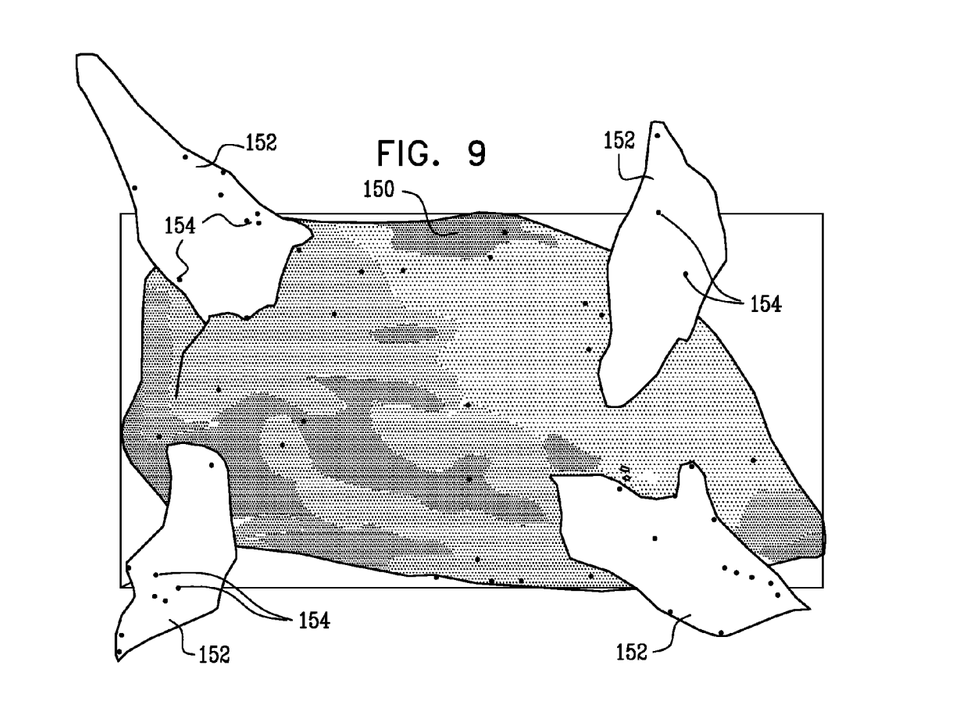
FIG. 9 is a schematic representation of an electro-anatomical map of a left atrium, including pulmonary veins connected to the atrium, in accordance with an embodiment of the present invention.

As another example, FIG. 9 is a schematic representation of an electro-anatomical map of a left atrium 150, including pulmonary veins 152 modeled by the method of FIG. 6, in accordance with an embodiment of the present invention. Map points 154 acquired by catheter 28 are marked on the surface of the atrium and the veins. (Unlike the model of FIGS. 7 and 8, only sparse map points were captured in the pulmonary veins in the typical clinical example that is shown in FIG. 9, leading to distortion in the model of the tubular shapes of veins 152.) The shading of the surface of the atrium is indicative of local values of a measured parameter related to electrical activity, such as electrical activation times.

Figure 10:
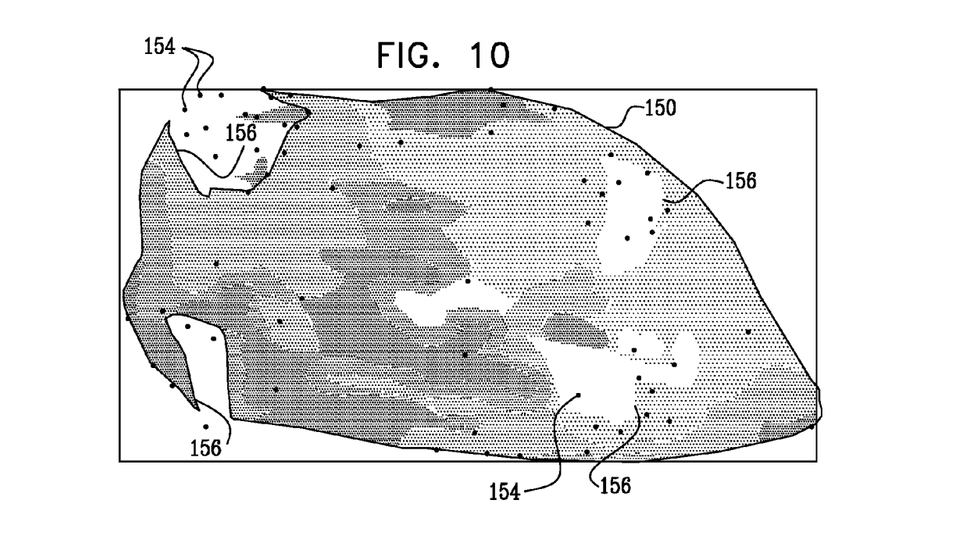
FIG. 10 is a schematic representation of the electro-anatomical map of FIG. 9, following removal of the pulmonary veins from the map, in accordance with an embodiment of the present invention.

FIG. 10 is a schematic representation of the electro-anatomical map of atrium 150 from FIG. 9, following removal of the pulmonary veins from the map at step 56 (FIG. 2), in accordance with an embodiment of the present invention. The areas of the ostia of the pulmonary veins are identified as entry areas 156. To separate the pulmonary veins from the map of the atrium, processor 36 detects the intersection lines of the meshes defining veins 152 with the mesh defining atrium 150. The processor then removes any parts of the meshes of the veins that are located inside the atrial cavity and closes the meshes of the veins for consistency.

FIG. 11 is a schematic representation of a pre-acquired CT image 160 of left atrium 80, which has been registered with an electro-anatomical map using the respective pulmonary vein models, in accordance with an embodiment of the present invention. Map points 162 from the electro-anatomical map are perfectly registered with the surface of the atrium in the CT image. The shading on atrium 80 represents electrical activation data, which are superimposed, following image registration, on the CT image.

Image Registration Using Landmarks Outside the Target Organ

This embodiment provides a method for registering a 3D pre-acquired image, such as a MRI, CT, PET or ultrasound heart model, acquired in an image coordinate system, with a real-time heart model created using a probe with a position sensing system. The real-time heart model may be generated, for example, either by electro-anatomical contact mapping or intra-cardiac ultrasound contours, as in system 20 (FIG. 1). Although the final result is a registered map and image of a heart chamber, the registration process uses landmarks that are not part of the heart itself.

Registration using landmarks outside the heart has several advantages:
- Landmarks in the blood vessels outside the heart chamber are relatively easy to find and identify with the catheter tip.
- As noted above, this method above can be carried out during passage of the catheter through a blood vessel into the heart, thus enhancing the safety and speed of the mapping procedure.
- Landmarks outside the heart do not move significantly during the heart cycle. Furthermore, the locations of vertically-oriented objects behind the heart, such as the ascending aorta and vena cava, are only slightly affected by respiratory movement. Registration of these relatively stationary landmarks with the pre-acquired image is easier and more reliable than registration of landmarks inside the heart.
- When the orientation of the pre-acquired image is known, a pair of landmarks may be sufficient to register the images. If the pre-acquired image is in DICOM (Digital Imaging and Communications in Medicine) format, for example, the image orientation may be provided by the DICOM header file. The position tracking capabilities of system 20 permit processor 36 to determine the orientation of the real-time image. The processor may use this information to align the orientation of the pre-acquired and real-time images, so that only translation, based on matching the pair of landmarks, is required to register the images.
- The user may weight the landmarks, so that different landmarks have different weights in the registration process, depending on the user's confidence in their accuracy, for example.

Figure 12A:
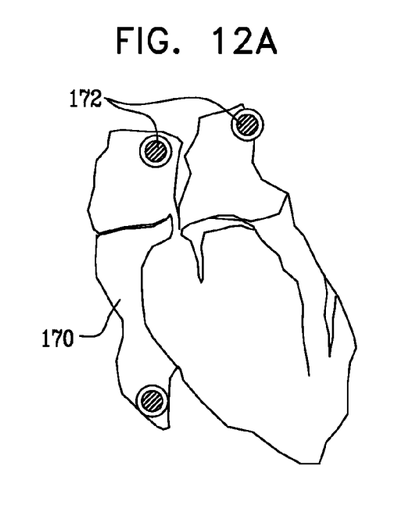
FIGS. 12A and 12B are schematic representations, respectively, of a pre-acquired image of the heart and of an electro-anatomical map of the heart, on which landmarks indicated by an operator have been superimposed, in accordance with an embodiment of the present invention.
Figure 12B:
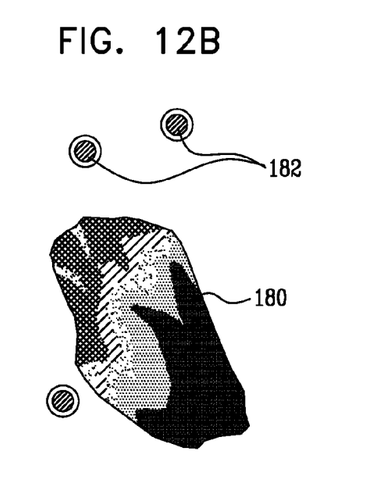

FIGS. 12A and 12B are schematic representations, respectively, of a pre-acquired image 170 of the heart and of an electro-anatomical map 180 of the heart, which are registered by landmark matching, in accordance with an embodiment of the present invention. In order to register images 170 and 180, the operator identifies an anatomical feature outside the heart that appears in the 3D image, to be used as a registration landmark. For example, the operator may choose a point or points 172 on the aorta, such as the bifurcations of the major vessels from the aortic arch. As another example, the operator may choose the ostia of the inferior or superior vena cava.

Operator 26 then maneuvers catheter 28 so that its tip contacts each of the landmark features in question, while indicating the corresponding location on the pre-acquired 3D image on display 38. Alternatively, when an ultrasound imaging catheter is used, the operator may maneuver the catheter so that the ultrasound beam acquires the required area of interest while indicating the corresponding location on the display. In the case of landmarks in a major blood vessel, such as the aorta or vena cava, the operator may perform this registration procedure while inserting the catheter through the blood vessel into the heart. As a result, the real-time image is already registered with the pre-acquired image when the catheter enters the heart to begin the mapping or intra-cardiac imaging procedure.

The landmark pair registration method can be used with various other landmarks. Some examples include:
- Registration of an electro-anatomical map of the left atrium using landmarks identified in the right atrium before transseptal entry into the left atrium.
- Registration of an electro-anatomical map using pacing electrodes in the patient's heart as landmarks.
- Registration of an electro-anatomical map using one or more landmarks in the esophagus. This variation requires that a catheter be inserted into the esophagus before (or after) mapping the heart.

Although the above embodiments use tubular objects in registering of pre-acquired and real-time images, the principles of tubular object recognition and processing that are described above may similarly be used in other applications, such as image enhancement and recognition, that do not necessarily involve registration of different images. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for imaging, comprising:
receiving a first three-dimensional (3D) image of a vicinity of an organ within a body of a subject;
converting the first 3D image to a half-edge data structure;
creating a geometrical model of a tubular structure in the first 3D image in the vicinity of the organ using the half-edge structure;
inserting an invasive probe into the organ;

capturing a second 3D image containing the organ using the invasive probe;

locating one or more points on a surface of the tubular structure using the invasive probe; and registering the second 3D image with the first 3D image by matching the one or more points to the geometrical model.

2. The method according to claim 1, wherein locating the one or more points comprises inserting the invasive probe into the tubular structure, and identifying the surface of the tubular structure while the invasive probe is inside the tubular structure.

3. The method according to claim 2, wherein identifying the surface comprises bringing the probe into contact with the one or more points, and determining coordinates of the probe.

4. The method according to claim 3, wherein locating the one or more points comprises receiving an input from a user marking the one or more points on the first 3D image.

5. The method according to claim 2, wherein inserting the invasive probe into the tubular structure comprises passing the invasive probe into the organ via the tubular structure.

6. The method according to claim 5, wherein the organ comprises a heart of the subject, and wherein the tubular structure through which the invasive probe is passed comprises a blood vessel that communicates with a chamber of the heart.

7. The method according to claim 1, wherein the geometrical model created of the tubular structure in the first 3D image is a first geometrical model, and wherein locating the one or more points comprises processing the second 3D image to create a second geometrical model of the tubular structure, and wherein matching the one or more points comprises fitting the second geometrical model to the first geometrical model.

8. The method according to claim 7, wherein capturing the second 3D image comprises generating an anatomical map of an inner surface of the organ by bringing the probe into contact with an inner surface of the organ at multiple locations on the inner surface, and recording position coordinates of the probe at each of the locations.

9. The method according to claim 8, wherein generating the anatomical map comprises producing an electro-anatomical map by measuring local electrical activity, using the probe, at the multiple locations, and wherein registering the second 3D image with the first 3D image comprises superimposing an indication of the local electrical activity on the first 3D image.

10. The method according to claim 7, wherein capturing the second 3D image comprises producing an ultrasound image of the organ using an ultrasound transducer in the probe, and wherein locating the one or more points comprises identifying the one or more points in the ultrasound image.

11. The method according to claim 1, wherein locating the one or more points comprises determining coordinates of the one or more points based on signals provided by a position sensor in the probe.

12. The method according to claim 1, wherein the tubular structure is outside the organ.

13. The method according to claim 12, wherein the organ is a heart of the subject, and wherein the tubular structure comprises a blood vessel in the vicinity of the heart.

14. The method according to claim 1, wherein creating the geometrical model comprises identifying a plurality of points appearing in the 3D image on a surface of the tubular structure, defining rings that pass through the points on the surface and encircle the tubular structure, and combining the rings to create the geometrical model.

15. The method of claim 1, further comprising:

passing the invasive probe through the tubular structure while inserting the invasive probe into the organ; and conducting the step of locating one or more points on the surface of the tubular structure using the invasive probe while passing the invasive probe through the tubular structure.

16. The method of claim 15, further comprising:

generating the second 3D image in real-time as the invasive probe is passing through the tubular structure.

17. The method of claim 15, wherein the tubular structure is outside the organ.

18. The method of claim 1, wherein the tubular structure is outside the organ, and the points located on the surface of the tubular structure are outside the organ.

19. A method for imaging, comprising:

receiving a three-dimensional (3D) image of a tubular structure in a vicinity of an organ within a body of a subject;

converting the 3D image to a half-edge data structure;

identifying a plurality of points appearing in the 3D image on a surface of the tubular structure;

defining rings, each ring passing through a respective subset of the points on the surface and encircling the tubular structure; and combining the rings to create a 3D geometrical model of the surface of the tubular structure and displaying the 3D geometrical model on a display.

20. The method according to claim 19, wherein defining the rings comprises specifying a starting point, and incorporating in the respective subset for each ring a group of the points that are equidistant from the starting point.

21. Apparatus for imaging, comprising:

an invasive probe, which is configured to be inserted into an organ within a body of a subject; and a processor, which is coupled to receive a first three-dimensional (3D) image of a vicinity of the organ, the processor being configured to convert the first 3D image to a half-edge data structure and to create a geometrical model of a tubular structure in the first 3D image in the vicinity of the organ, the processor being further configured to capture a second 3D image containing the organ using the invasive probe, and to locate one or more points on a surface of the tubular structure using the invasive probe, and to register the second 3D image with the first 3D image by matching the one or more points to the geometrical model.

22. The apparatus according to claim 21, wherein the invasive probe is configured to be inserted into the tubular structure, and wherein the processor is configured to identify the surface of the tubular structure while the invasive probe is inside the tubular structure.

23. The apparatus according to claim 22, wherein the invasive probe comprises a position sensor, and wherein the processor is configured to identify the surface by determining coordinates of the probe, using the position sensor, while the probe contacts each of the one or more points.

24. The apparatus according to claim 23, and comprising a user input device, wherein the processor is coupled to receive an input from a user via the user input device marking the one or more points on the first 3D image.

25. The apparatus according to claim 21, wherein the geometrical model created of the tubular structure in the first 3D image is a first geometrical model, and wherein the processor is configured to process the second 3D image to create a second geometrical model of the tubular structure, and to fit the second geometrical model to the first geometrical model.

26. The apparatus according to claim 25, wherein the second 3D image comprises an anatomical map of an inner surface of the organ, which is generated by bringing the probe into contact with an inner surface of the organ at multiple locations on the inner surface, and recording position coordinates of the probe at each of the locations.

27. The apparatus according to claim 25, wherein the invasive probe comprises an ultrasound transducer, and wherein the second 3D image comprises an ultrasound image of the organ that is captured using the ultrasound transducer in the probe, and wherein the one or more points are located by identifying the one or more points in the ultrasound image.

28. A computer software product, comprising a non-transitory computer-readable medium in which program instructions are stored, which instructions, when read by a computer, cause the computer to receive a first three-dimensional (3D) image of a vicinity of an organ within a body of a subject, to convert the 3D image to a half-edge data structure, to create a geometrical model of a tubular structure in the first 3D image in the vicinity of the organ, to capture a second 3D image containing the organ using an invasive probe that is inserted into the organ, to locate one or more points on a surface of the tubular structure using the invasive probe, and to register the second 3D image with the first 3D image by matching the one or more points to the geometrical model.

29. A computer software product, comprising a non-transitory computer-readable medium in which program instructions are stored, which instructions, when read by a computer, cause the computer to receive a three-dimensional (3D) image of a tubular structure in a vicinity of an organ within a body of a subject, to convert the 3D image to a half-edge data structure, to identify a plurality of points appearing in the 3D image on a surface of the tubular structure, to define rings, each ring passing through a respective subset of the points on the surface and encircling the tubular structure, and to combine the rings to create a 3D geometrical model of the surface of the tubular structure.

* * * * *